(12) United States Patent
Martin

(10) Patent No.: US 6,729,175 B2
(45) Date of Patent: May 4, 2004

(54) TEST PIECE FOR INSPECTION PENETRANT PERFORMANCE ASSESSMENT AND COMPARISON

(75) Inventor: William J. Martin, Downey, CA (US)

(73) Assignee: Sherwin, Inc., South Gate, CA (US)

(*) Notice: Subject to any disclaimer, the term of this patent is extended or adjusted under 35 U.S.C. 154(b) by 216 days.

(21) Appl. No.: 10/044,238

(22) Filed: Jan. 14, 2002

(65) Prior Publication Data

US 2002/0059711 A1 May 23, 2002

(51) Int. Cl.[7] .......................... G01N 21/93; B23P 25/00
(52) U.S. Cl. ........................................ 73/1.04; 29/896.6
(58) Field of Search .............................. 73/1.04, 1.01; 250/252.1 A, 252.1 R; 234/1; 29/896.6, 407.01, 557, 558, DIG. 26, DIG. 33

(56) References Cited

U.S. PATENT DOCUMENTS

| | | | |
|---|---|---|---|
| 3,946,597 A | * | 3/1976 | Tahbaz ..................... 73/104 X |
| 4,078,417 A | | 3/1978 | Shigewawa |
| 4,610,157 A | | 9/1986 | Vicki et al. ............... 73/104 X |
| 4,895,750 A | * | 1/1990 | Pratt ......................... 73/608 X |
| 5,113,422 A | * | 5/1992 | Pinder ......................... 378/58 |

* cited by examiner

Primary Examiner—Thomas P. Noland
(74) Attorney, Agent, or Firm—Edbar W. Averill, Jr.

(57) ABSTRACT

A test panel and process of preparing a test panel for evaluating the performance of inspection penetrants by inducing cracks into a brittle coating. The process includes drilling one or more holes from the back side of a test plate which has been plated on a plated side. The holes are drilled partway through the test plate and create cavities. A penetrating tool which has a point is inserted into a cavity and the point is pressed in a slow measured manner from the back side of the panel which has a brittle plated coating on the front side to be cracked. The result is a series of cracks formed in an area opposite the area of the cavity.

7 Claims, 3 Drawing Sheets

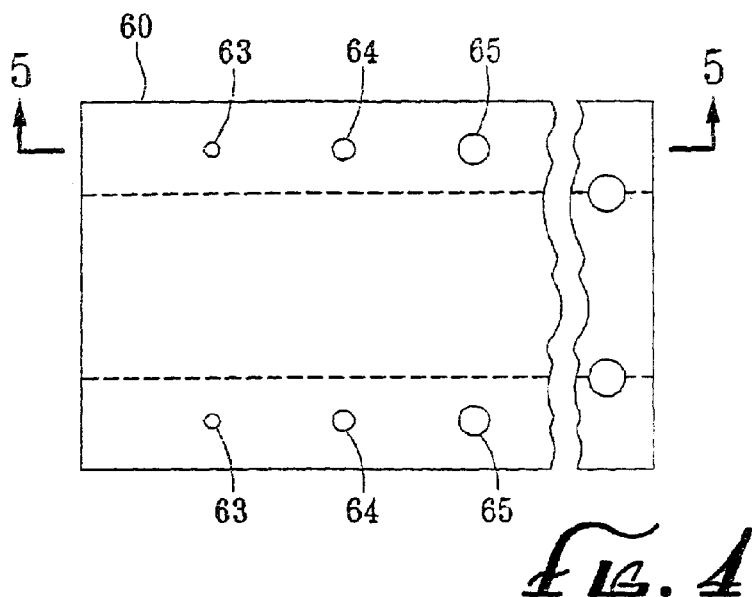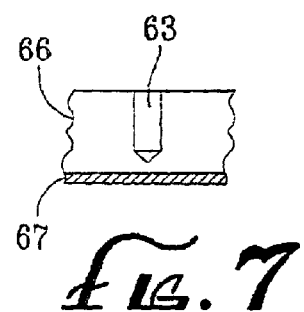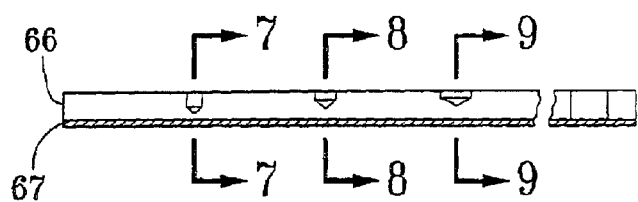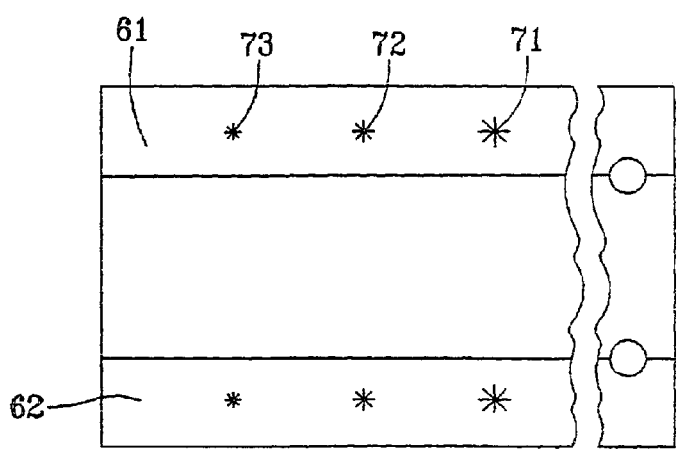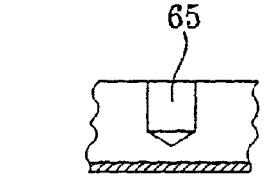

TEST PIECE FOR INSPECTION PENETRANT PERFORMANCE ASSESSMENT AND COMPARISON

CROSS REFERENCE TO RELATED APPLICATION

This application is related to applicant's application Ser. No. 09/197,884, filed Nov. 23, 1998, by the present applicant and which has issued as U.S. Pat. No. 6,311,538.

BACKGROUND OF THE INVENTION

Inspection penetrants are used to find surface cracks in all types of insoluble materials, but primarily in nonmagnetic metals, such as aluminum, high nickel alloy, stainless steel and titanium. These metals predominate in the aerospace industry. On many aerospace parts, such as rotating discs of turbine engines, even the most microscopic cracks must be found, as these microscopic cracks will propagate under the stresses and loads placed on them during operation. Propagation can be extremely rapid and part failure sudden and catastrophic.

Inspection of such critical parts for surface cracks, whether newly manufactured or parts that have been in service, is accomplished with fluorescent penetrants. The process consists of application of fluorescent penetrant, an oily-like fluid charged with fluorescent dyestuff, to the surface of the part by immersion, brushing or spraying; allowing the fluorescent penetrant to remain on the surface for sufficient time to enter microscopic surface openings by capillary action; removing the penetrant that did not enter cracks and surface flaws from the surface by washing with a pressure rinse of plain water or with the aid of a detergent or emulsifying agent. The part is then dried in an oven and typically a developing agent is applied to bring the crack entrapped fluorescent penetrant back to the surface so it may be seen as a glowing line under ultraviolet light (black light) in a darkened room.

The fluorescent penetrant system must function properly or cracks will go undetected. These cracks can propagate into catastrophic failures. For example, if the penetrant has become contaminated with different substances, its fluorescing properties will be diminished. If the mechanism for applying the developing agent is malfunctioning, the flaws will not be clearly identifiable under the ultraviolet light. There are other causes for failure such as rinse water with a too-high temperature and a too-high concentration of detergent which will prematurely remove penetrant from cracks.

To defend against processing critical aerospace and turbine engine parts in a malfunctioning fluorescent penetrant system, a general requirement is to prove the system each day before it is used by processing a test panel with known defects. If, after processing, these known defects are not displayed as anticipated, i.e. with the same completeness and brilliance as in previous tests, this alerts the operator of the need to check the system for a malfunction.

Probably the best known panel for this purpose, and most widely used, is the PSM-5 panel manufactured by Sherwin Incorporated, South Gate, Calif., to Pratt & Whitney drawing TAM 146040, which drawing is dated April 1975. The PSM-5 panel is a 4×6" piece of stainless steel, thickness 0.090" with a strip of hard chrome plate running lengthwise down one side. The thickness of this chrome plate is 0.003" or greater. As hard chrome plating is applied electrolytically, its thickness will vary over the surface with heavier coating to be anticipated at the edges. Five cracks of varying magnitude, evenly spaced, are induced by exerted pressure opposite the hard chrome strip with a Brinell hardness test instrument. The balance of the front of this test piece and adjacent the chrome strip is a rough area obtained by grit blasting with aluminum oxide or other media.

The most difficult task in manufacturing the PSM-5 panel is in the formation of the smallest crack, a crack diameter in the range of 0.015" to 0.030". This small crack, necessary to verify the system's ability to find the truly microscopic crack, is difficult to produce, as there is no room for the slightest error in the plating composition or in the pressure exerted by the hardness tester. The crack is formed by pressure exerted by a hard round ball on the side opposite to the plating. The plating side is backed up against a selected surface. The pressure is measured by weight, pounds or kilograms. Although the hardness test equipment includes an instrument to indicate in kilograms the weight force, there is a lag in indication and this equipment is not sufficiently precise to give controlled crack formation in the area of small cracks whose detection is required by today's advanced industry.

The method of inducing cracks with a hardness tester has an inherent deficiency. If the induced crack fails to meet its specification, it is not possible to review and remeasure to verify if the prescribed pressure was applied. The indentation left by the hardness tester is not measurable with ordinary tools.

As the aerospace industry continues to reduce the weight of their vehicles while at the same time demanding higher performance and placing greater stress loads on the components, the need for the penetrant process capability to locate smaller surface flaws becomes more critical. The need for a test piece that verifies the inspection system's capability to meet these more demanding specification requirements is obvious.

No two PSM-5 panels are exactly alike. They are produced individually. Further, the cracking method cannot be precisely controlled. It is not possible to hold two PSM-5 panels side-by-side and expect to see equivalency in the crack patterns. The PSM-5 panel cannot be used to reliably compare relative sensitivity between two different penetrants because no two panels are equivalent. One cannot expect to process one panel with new penetrant and another with in-use penetrant and obtain a meaningful comparison. This is due in part to the fact that the panels are produced separately and not as one piece. It is also due to the method of cracking, applying pressure until cracking occurs.

Recognizing this deficiency in the PSM-5 panel, governing agencies now require the user of the PSM-5 panel to photograph the panel when first processed with unused penetrant materials in the laboratory and, then to use this photograph to compare results obtained when the panel is subsequently processed through the production penetrant system on a daily basis. Although this has some utility, it is not truly satisfactory, since, in order to take photographs under ultraviolet light, time exposures are required and the photographed fluorescent crack indications will vary in size and definition with exposure time, as well as with film negative and printing paper and technique. Further the photograph must be viewed under white light, as the crack indications in the photograph do not fluoresce. The panel itself must be read under ultraviolet light. Such indications cannot be viewed and compared to actual fluorescing indications in the darkened inspection booth where the lighting is ultraviolet and be meaningful.

But this recently imposed requirement of a photographic comparison in such specifications as ASTM E 1417, despite its inadequacies, is evidence of the need of a reference point when interpreting the panel's results.

Also, although the PSM-5 cracks may be small, e.g. 0.015" of an inch in diameter, their depth is the depth of the plating which is 0.003" or greater. The nature of the hard chrome requires a plating thickness of close to 0.003" to crack with a pressure load, otherwise, it stretches until it splits uncontrolled. A crack 0.003" or more in depth retains considerable penetrant and, therefore, does not reveal abusive over-washing and over-heating in processing as readily as it should. Further, a crack with this depth tends to retain penetrant even when subjected to extensive cleaning between tests. Such retained penetrant from a previous test leads to erroneous conclusions on subsequent tests. ASTM E 1417 stresses the need for adequate cleaning of the known defect standard between tests.

To meet today's need, the brittle coating must lend itself to controlled cracking in thin coatings, less than 0.002". Thin coats of chrome plating, such as 0.001", do not crack uniformally even though pressure exerted is uniform. Although there may be a place for chrome plating, metal conversion coatings, silicate and other brittle coatings, and these coatings lend themselves to the controlled method of cracking that I discovered, my favorite brittle coating is nickel plate, either electrolytic or electroless nickel type, because a thin coat of nickel plate lends itself to controlled cracking. Cracks can be induced with my invention in nickel plate in a coating as thin as 0.00025" in a controlled manner.

Although we have fabricated panels with plating thickness of 0.00025" which have proven to be a practical tool, typically, we have found the plating thickness of 0.001" the most useful. Cracks of this depth duplicate the small shallow cracks which are the object of today's most exacting inspections. The penetrant retained in a crack reservoir 0.001" deep with a diameter of 0.015" is sufficiently minuscule for the entrapped penetrant to be affected deleteriously by overwashing, over-heating and inadequate developer application. Abusive processing or a substandard penetrant material is more readily apparent with a test piece with shallow, 0.001" cracks than when crack depth of the test piece is 0.003" or greater.

An added advantage of the thinner coating is the ease of cleaning the panel and freeing the crack reservoirs of materials deposited during previous use. A 15 minute soak in alcohol is all that is required to clear the reservoirs whereas a lengthy bath in an ultrasonic cleaning tank charged with a chlorinated solvent often has to be repeated to clear the crack reservoirs of the PSM-5 panel.

Like the PSM-5 test piece, my favorite substrate is stainless steel, as it is rugged in construction, not subject to corrosion, and withstands the rough handling when sent through the penetrant system.

There are other test pieces used to evaluate inspection penetrants, such as thermally cracked aluminum blocks and "nickel-chrome" test panels. These panels are not suitable replacements for the PSM-5 type panel and are not intended for use in evaluating the functioning of an inspection penetrant system.

The nickel-chrome test panel for the sake of clarification should be described, so it will be understood that it does not compete with our invention. It is known in the industry as the "twin nickel-chrome panel." This panel's substrate is brass, subject to corrosion. The plating is brittle nickel with a flash of chrome. Panels usually measure about 1¼×4" and are 0.06 thick. The plating will vary in thickness from as thin as 0.0002" (5 μm) to 0.002" (50 μm).

The panels are bent over curved anvils to induce cracking and then straightened, as shown in U.S. Pat. No. 4,610,157. The main difficulty with the "twin nickel-chrome panel" is the form of the cracks, straight cracks, running laterally from one edge of the test piece to the other edge. The cracks' geometries are open troughs. Penetrant that enters this type of cracking is easily flushed through the open trench or trough. While it is possible to compare the visibility of two penetrants by judicious removal of surface penetrant, it is not possible to process these test pieces in the work environment. The penetrant flushes from the "troughs" too readily. These test pieces have a limited function. For this and other reasons, they are not a practical tool for monitoring a penetrant system. The "twin nickel-chrome panel" is primarily a laboratory tool. Another patent which shows a test panel process is U.S. Pat. No. 4,078,417.

The nickel-chrome test panel is normally produced as a single panel which is later sheared into matching panels. It can be used for side-by-side comparisons of different penetrant materials in the laboratory. It is not sufficiently rugged to be used to measure the capability of a production penetrant system and it gives erroneous data relative to the wash cycle.

The present continuation in part application is concerned with the means to further control the magnitude of the induced cracks made in the test piece. The objective of the improved process is to manufacture test pieces with precise crack sizes, both in crack depth and crack length. The use of the penetration method described in the present application has made possible precision induced cracking in the production of virtual twin test pieces where a single brittle coating specimen is shared into equivalent sections as the brittle plating coating is applied at the same time on both sections. However, it has been difficult or impossible to extend this control when the plating differs, which is the case with specimens plated at different times. The present improvement makes possible such depth and length control by confining the cracking force to a predetermined limited area by weakening the substrate to such a predetermined limited area.

SUMMARY OF THE INVENTION

It was discovered that by drilling holes part way through the substrate from the back of the substrate toward the plated side, cracks could be induced in a much more controlled area, namely, the area equal to the diameter of the hole which has been drilled part way through the substrate. The tool used to produce cracking described in the present application is inserted in the incompletely drilled holes and forced against the bottom of the hole an amount sufficient to create cracks in the plated surface on the plated side of the test plate. The result was a highly controlled crack depth and length which did not require the plating of other panels to be done at the same time.

The present invention is for a method of forming controlled cracks in a predetermined area of brittle plating on a plated surface of a test plate which comprises a substrate which has a plated area on a plated side and a back side. One or more holes are drilled part way through the substrate from the back side of the test plate opposite a plated area of the test plate to create a cavity having a cavity diameter and a cavity bottom. The point of a hardened tip is inserted into the cavity and forced against the cavity bottom with sufficient force to create a deformation of a portion of the plated area beneath the cavity bottom. This forms a plurality of cracks in the plated area limited to an area no larger then the cavity diameter. Preferably, holes of different sizes are drilled in the test plate to provide cracks of different depth and length. The holes are preferably drilled more than half way through the substrate.

BRIEF DESCRIPTION OF THE DRAWINGS

FIG. 4 is a plan view of a test plate as viewed from the back side with two sets of three drilled cavities therein.

FIG. 5 is a cross-sectional view taken along line 5—5 of FIG. 4.

FIG. 6 is a bottom view of the test plate of FIG. 4.

FIG. 7 is a cross-sectional view taken along line 7—7 of FIG. 5.

FIG. 8 is a cross-sectional view taken along line 8—8 of FIG. 5.

FIG. 9 is a cross-sectional view taken along line 9—9 of FIG. 5.

FIG. 10 is an enlarged cross-sectional view of a cavity with a hardened tip inserted therein.

DESCRIPTION OF THE PREFERRED EMBODIMENTS

Figure 1:
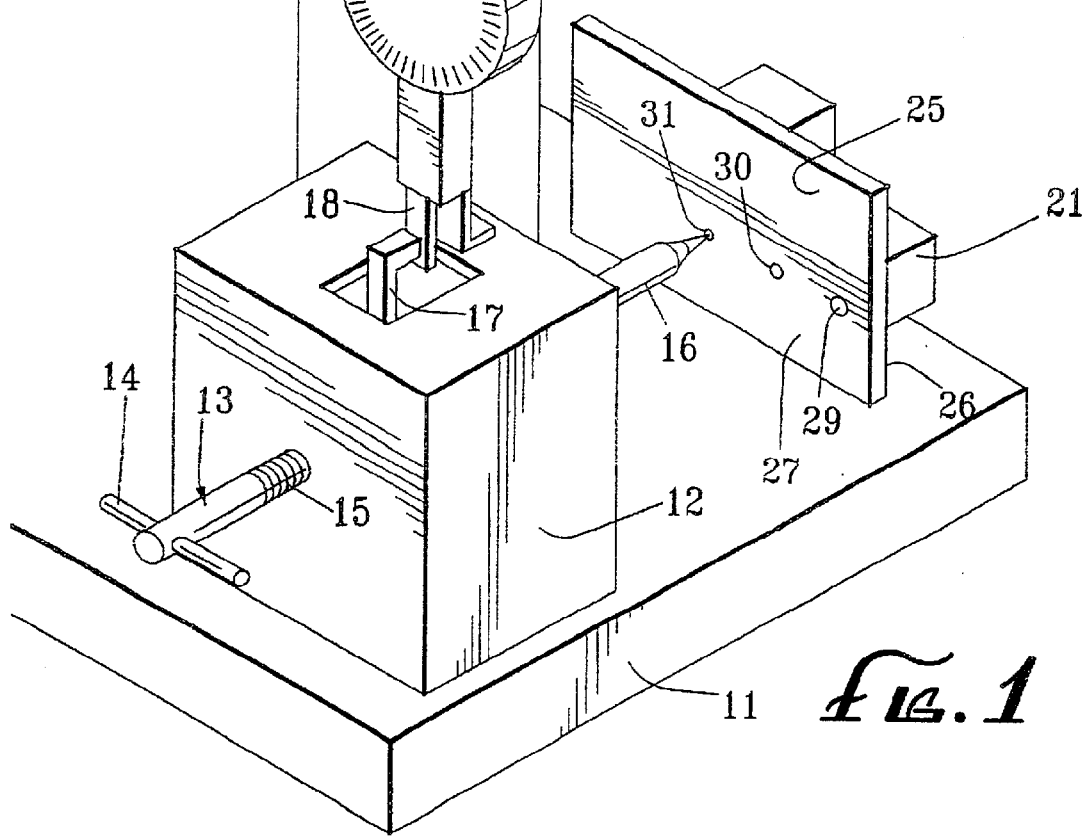
FIG. 1 is a perspective view of the tool used in the process of the present invention together with a test panel being formed.

The tool of the present invention is shown in FIG. 1 and indicated generally by reference character 10. The tool has a frame 11 which supports a block 12. Block 12 holds a manually turned penetrating assembly 13 which has a handle 14, a threaded shaft 15 and a penetrating tool point 16. A finger 17 moves with the threaded shaft 15 and the penetrating point 16. Finger 17 presses against the measuring arm 18 of dial test indicator 19. Dial test indicator 19 is held by an arm 20 which is secured to frame 11. Frame 11 also holds a backing block 21. Backing block 21 has a cavity into which an anvil (not shown) is held.

The important feature of the process of the present invention is to control the depth of the penetration of point 16 into the test plate or panel 25. Panel 25 is preferably stainless steel including 316, 321 and 18-8 and panel 25 has a plated side 26 and an uncoated side 27. The plating can be formed by hard chrome, electrolytic nickel and electroless nickel to a thickness of between 0.0002" and 0.002". This plating forms a brittle coating in which cracks form when the back surface is penetrated by point 16. By moving the point 16 into contact with the uncoated side 27, zeroing the dial test indicator 19 and measuring the distance of penetration, a highly controlled series of cracks is formed. For example, penetration to a depth of 0.016" is typical to make a crack with a diameter area of 0.015". Most commonly, five craters such as craters 29, 30 and 31 of FIG. 1 are formed of increasing depths equally spaced along panel 25.

The industry also requires a test piece for comparing penetrant sensitivity. Such panels are shown in FIG. 3 and are formed from a single panel shown in FIG. 2. In the past, twin nickel chrome panels have been made by plating a brass panel which is then bent over an arbor which induces lateral cracking. The plated brass is then straightened and sheared into two equivalent pieces. Because these cracks run laterally, they are in effect troughs which are open at both ends. Such open troughs tend to be too easily flushed by normal processing and thus, have limited practical function. The test panels of the present invention do much more to monitor the system in that they compare visibility after production-type processing, they compare washability with the grit-blasted roughened area, and provide an accurate control during production. These panels are made preferably using an electroless plated primary nickel, but with a higher percentage of phosphoric acid than normal. The addition of phosphoric acid gives added brittleness to the coating making it possible for crack plating with a thickness as thin as 0.0002" (5 micrometers). The point 16 is preferably round rather than a depressed oval as formed by a Brinell hardness tester. Furthermore, the method of inducing cracks of the present invention permits the accurate reinsertion of the needle-like instrument that initially formed the round hole if it is necessary to increase the magnitude of the cracking. In the past, there has been considerable difficulty in producing this smallest diameter crack, the one measuring 0.015" or less.

Figure 2:
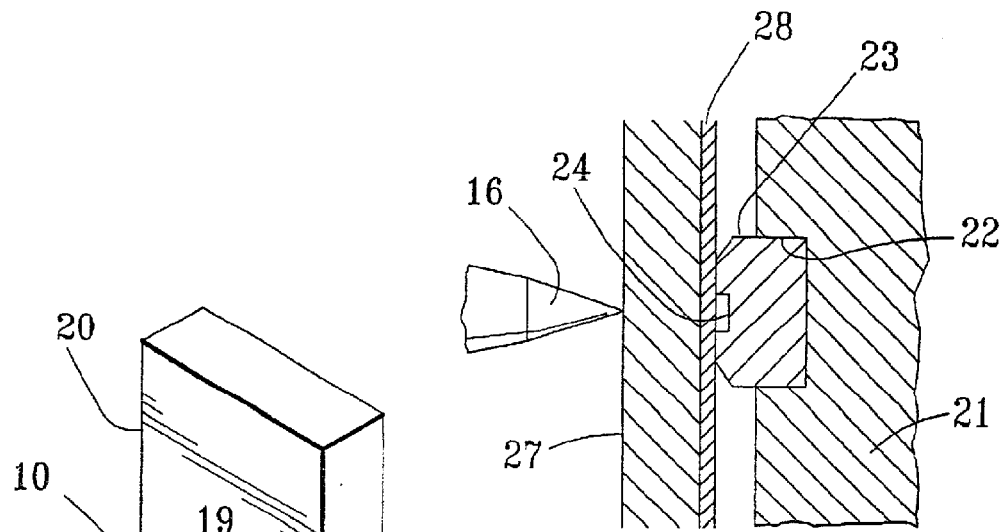
FIG. 2 is a front view of the plated side of a test plate made according to the process of the present invention.
Figures 3A, 3B:
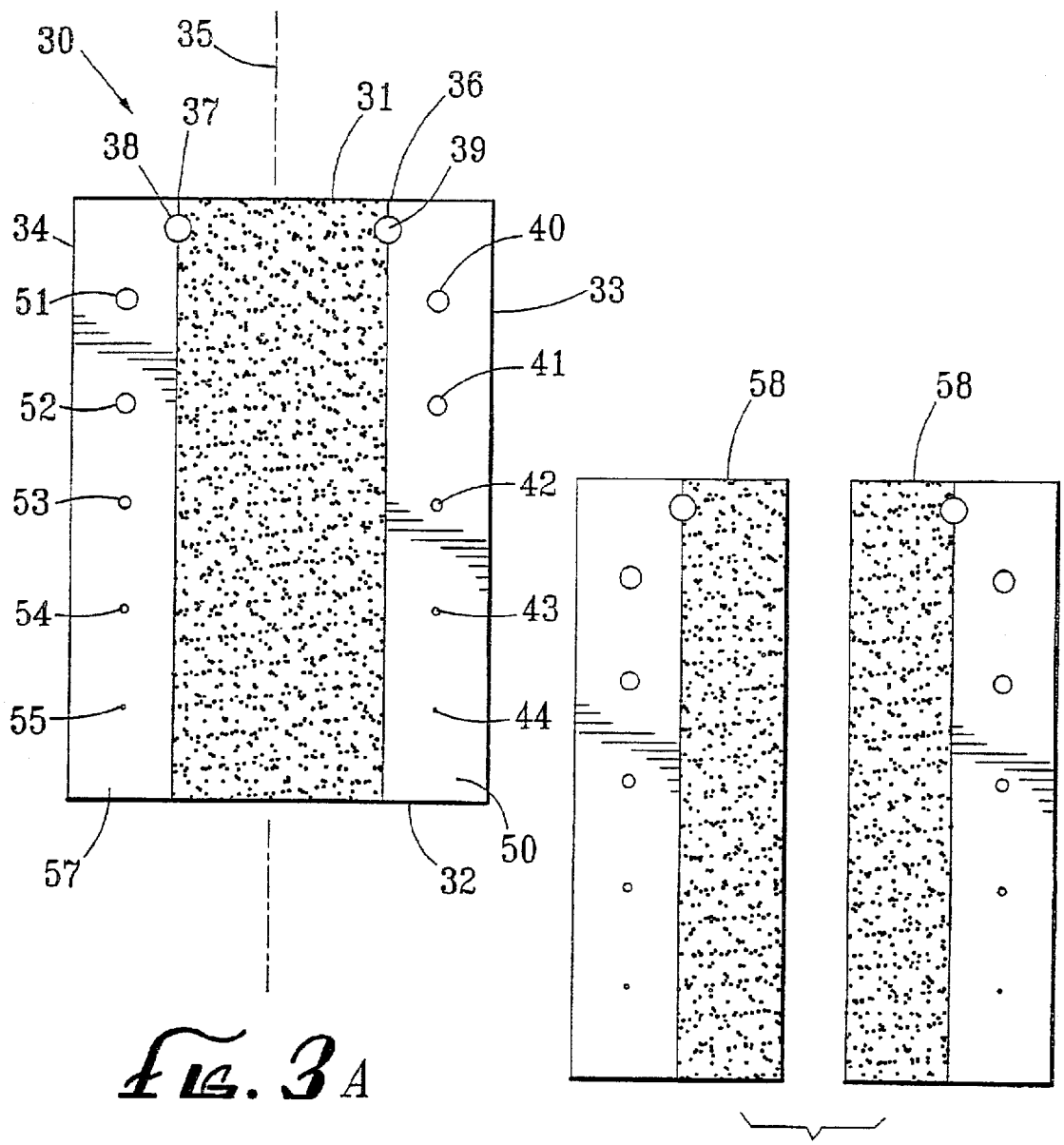
FIG. 3 is a front view of the plated side of the test plate of FIG. 2 sheared into two individual test plates.

As shown in FIG. 2, panel 30 is a rectangular plate having a top edge 31, a bottom edge 32, a right side 33 and a left side 34. Panel 30 has positioned midway between the right side and the left side. A first middle zone 36 is located between vertical center 35 and right side 33, a second middle zone 37 is located between vertical center 35 and left side 34. The area between the first and second middle zones 36 and 37 has been grit-blasted and a pair of support holes 38 and 39 have been formed one-fourth way in from the right side and the left side. The area between the first middle zone 36 and right side 33 and second middle zone 37 and left side 34 are simultaneously plated, preferable with electroless plating, primarily nickel, but with a high percentage of phosphoric acid. Then a series of increasing cracks 40, 41, 42, 43 and 44 are formed in the brittle plated area 50. Similarly, cracked areas 51, 52, 53, 54 and 55 are formed by the above-described process in brittle plated area 51.

Next, as shown in FIG. 3, the panel 30 is sheared into two panels 52 and 53 which are nearly identical since they were plated at the same time from the same sheet. These panels, therefore, become very useful in the twin panels test.

A panel 60 is shown in FIG. 4 from the back side. Panel 60 has two plated areas 61 and 62 shown in FIG. 6 and indicated by phantom lines in FIG. 4. Three cavities comprising a smallest cavity 63, intermediate cavity 64, and a largest cavity 65, are drilled part way through panel 60 in an area adjacent plated areas 61 and 62. These cavities are shown in cross-sectional view in FIGS. 7, 8, and 9. For instance, in FIG. 7 it can be seen that hole 63 passes through a majority of the substrate 66, but does not enter the plated area 67. For a substrate of 3/32 thickness and a plated area of between 0.001 and 0.002 inches thick, hole 63 passes a depth of about 0.007 leaving a thickness of substrate and plating between 0.022 and 0.025 inches.

As shown in FIG. 10, a hardened tip 68 having a point 69 has been inserted into cavity 65 and forced downwardly against backing block 70. This forms a cracked area 71 having a required diameter controlled by the diameter D of cavity 65. Cracked areas 71, 72, and 73 are shown in FIG. 6 and correspond approximately to the diameter of the cavities 65, 64, and 63, respectively.

Because of the accurate limitation of the resulting crack depth and crack length, the test plate can be created which provides a very reproducible result as a standard. The hole gives better control of the crack pattern. Without the hole, the crack can get too big. With the hole, the crack pattern generally does not exceed the hole diameter.

The present embodiments of this invention are thus to be considered in all respects as illustrative and not restrictive; the scope of the invention being indicated by the appended claims rather than by the foregoing description. All changes which come within the meaning and range of equivalency of the claims are intended to be embraced therein.

I claim:

1. A method of forming controlled cracks in predetermined areas of a brittle plating of a test plate, said test plate having a substrate which has a plated area on a plated side and a back side, said method comprising:

drilling a hole partway through said substrate from the back side of said test plate opposite an area which is plated on the plated side thereby creating a cavity having a cavity diameter and a cavity bottom;

inserting a point of a hardened tip into said cavity;

forcing said point against said cavity bottom with sufficient force to create a deformation of a portion of said plated area beneath said cavity bottom thereby forming a plurality of cracks in said plated area limited to an area no larger than and controlled by the cavity diameter.

2. The method of forming controlled cracks of claim 1 wherein a plurality of holes of differing diameters are drilled partway through said substrate and a point of a hardened tip is inserted into and forced against the resulting cavity bottoms to form a plurality of cracks at locations opposite each of said plurality of holes.

3. The method of forming controlled cracks of claim 1 wherein said point of said hardened tip is forced a predetermined distance against said cavity bottom.

4. The method of forming controlled cracks of claim 1 wherein said substrate has a thickness of about three thirty seconds of an inch thick and said hole is drilled more than half way through said substrate.

5. The method of forming controlled cracks of claim 4 wherein holes of at least three different diameters are drilled partway through said substrate comprising a hole of the smallest diameter, an intermediate diameter and the largest diameter.

6. The method of forming controlled cracks of claim 5 wherein the hole of the smallest diameter is drilled furthest into said substrate, the hole of intermediate diameter is drilled an intermediate distance into said substrate and the hole of largest diameter is drilled the least distance into said substrate.

7. The method of forming controlled cracks of claim 6 wherein the hole of the largest diameter is drilled about half way through said substrate.

* * * * *